United States Patent [19]
deWinter

[11] 4,261,834
[45] Apr. 14, 1981

[54] DEVICE AND PROCESS FOR REMOVING PYROGENS FROM AQUEOUS SOLUTIONS

[75] Inventor: Dirk M. deWinter, Belmont, Mass.

[73] Assignee: Millipore Corporation, Bedford, Mass.

[21] Appl. No.: 906,922

[22] Filed: May 18, 1978

[51] Int. Cl.$^3$ .................. B01D 31/00; B01D 13/00
[52] U.S. Cl. .................. 210/651; 210/500.2; 210/490; 210/433.2
[58] Field of Search .......... 210/22, 23 F, 23 H, 210/321 R, 335, 339, 489, 490, 500 M, 433 M, 346

[56] References Cited
U.S. PATENT DOCUMENTS

| | | | |
|---|---|---|---|
| 3,120,489 | 2/1964 | Hoch | 210/339 X |
| 3,238,056 | 3/1966 | Pall et al. | 210/505 X |
| 3,573,158 | 3/1971 | Pall et al. | 210/505 X |
| 3,598,728 | 8/1971 | Bixler et al. | 210/22 |
| 3,615,024 | 10/1971 | Michaels | 210/490 |

*Primary Examiner*—Frank A. Spear, Jr.
*Attorney, Agent, or Firm*—Edward S. Irons; James R. Laramie

[57] ABSTRACT

Pyrogens can be effectively removed from an aqueous solution by passing a stream of the solution through a device comprising at least two anisotropic ultrafiltration membranes positioned in series, said membranes having nominal molecular weight limits less than the molecular weight of the pyrogens, including aggregates or micelles thereof, to be removed, wherein at least one membrane is juxtaposed with at least one other membrane so that substantially all of the skin surface of one membrane is in intimate contact with substantially all of the skin surface of the other membrane and wherein the edges of one membrane are sealed to the corresponding edges of the other membrane.

13 Claims, 7 Drawing Figures

DEVICE AND PROCESS FOR REMOVING PYROGENS FROM AQUEOUS SOLUTIONS

BACKGROUND OF THE INVENTION

1. Field of the Invention

This invention relates to a device for effectively removing pyrogens from aqueous solutions.

2. Description of the Prior Art

Pyrogens, the protein organic matter or complex polysaccharide of a fever producing nature frequently found in sterile water, are produced by a certain group of bacteria which enter and develop in water during distillation and subsequent storage. During sterilization they are killed leaving their bodies and products of decomposition in the solution. They are said to be responsible for the majority of reactions following intravenous injections. The entity primarily responsible for pyrogenic reactions in mammals is the lipopolysaccharide (LPS) from Gram-negative bacteria. A comprehensive discussion of lipopolysaccharides and the pyrogenic response can be found in Good, C. M., et al., "I. The Biochemistry of Pyrogens", Bulletin of the Patenteral Drug Association, vol. 31, no. 3 (1977).

Prior to the present invention, water for injection was prepared using relatively expensive distillation and reverse osmosis equipment which was not wholly effective in the removal of pyrogens. It has been found that pyrogens are quantitively removed by a pinhole-free assymetric ultrafiltration membrane. An ultrification membrane, often referred to as an anisotropic or "skinned" membrane, consists of a thin polymeric film or skin supported on or bonded to a highly porous substrate. The substrate contributes strength and durability to the filter, but the thin skin is the actual molecular filtration membrane. The skin layer is densely structured to retain molecules, but because it is very thin, typically less than 2 microns, the resistance to flow caused by the dense structure is minimized. Since the skin is backed by a very open, porous substrate layer, flow rates through the filter are high.

Skinned membranes retain most molecules above a nominal limit as well as some fraction of smaller molecules. They do not retain all molecules larger than an absolute cut-off size. Although several factors affect the ability of a molecule to pass through a skinned membrane, the efficiency of retention for a particular solute is primarily determined by the size and shape of the solute molecules. However, because it is not possible to detect discrete pores in skinned membranes which can be measured accurately and it is difficult to measure the apparent diameter of most large molecules in solution, meaningful size limits cannot be assigned to skinned membranes. Since molecular weight is an approximate guide to molecular size, skinned membranes can be conveniently characterized by their percent retention of selected solutes of globular proteins having accurately known molecular weights. From these data, each membrane can be assigned a nominal molecular weight limit (NMWL), i.e. a molecular weight at and above which most species are efficiently retained by that membrane.

The removal of pyrogens required for water for injection is 5 orders of magnitude or 99.999 percent. For such reduction, only $10^{-5}$ part of the flow should be allowed to pass through the pinholes of an otherwise pyrogen excluding ultrafiltration membrane. Ultrafiltration membranes containing pinholes and other inherent defects remove about 3 orders of magnitude of pyrogens from aqueous solutions. It is extremely difficult to make large areas of an ultrafiltration membrane pinhole-free, and even if it were possible to make one completely pinhole-free, the cost would be prohibitive.

SUMMARY OF THE INVENTION

The disadvantages and limitations of the prior art methods for pyrogen removal have been alleviated by the present invention. It was determined that, since it is possible to remove about 3 orders of magnitude of pyrogens from an aqueous solution using a presently available ultrafiltration membrane, two such membranes placed in series should initially remove about 6 orders of magnitude. However, as the pyrogen concentration builds up between the two membranes, the amount of pyrogens removed from the water will drop off. It is important, therefore, to eliminate the volume between the two membranes in series. By placing the membranes "skin-to-skin", i.e. juxtaposed so that substantially all of the skin surface of one membrane is in intimate contact with substantially all of the skin surface of the other membrane, there is no volume between the membranes, and thus, no place for accumulation of pyrogens. If the two membranes are placed adjacent to one another but not skin-to-skin, the open porous substructure of the membrane affords sufficient volume for accumulation. More significantly, however, by placing two ultrafiltration membranes in intimate contact skin-to-skin so that the pinhole-free portions of one membrane block the pinholes of the other, the volumetric flow through the pinholes is statistically reduced by the ratio of the cumulative exposed area of pinholes to the corresponding intact membrane area. Using skin-to-skin mutual pinholes shielding, 5 orders of magnitude of pyrogens, including aggregates or miscelles thereof, can be reliably removed.

Exposure of the porous substructure of the upstream membrane of two membranes placed skin-to-skin and positioned in a stream of an aqueous solution may result in the accumulation of debris in the substructure and the lowering of flux through the membranes. By placing a third membrane with its skin adjacent to the feed stream, it was observed that the performance in pyrogen removal and throughput was superior to the two membrane system.

DESCRIPTION OF THE PREFERRED EMBODIMENTS

In accordance with the present invention, pyrogens including aggregates or micelles thereof, can be effectively removed in the preparation of water for injection by passing a stream of an aqueous solution through at least two anisotropic ultrafiltration membranes, one of which having substantially all of its skin surface in intimate contact with substantially all of the skin surface of another with corresponding edges of each membrane being sealed together. Using this skin-to-skin membrane configuration, 99.999 percent pyrogen removal can be consistently obtained.

Because of the mutual pinhole shielding with results from this skin-to-skin configuration, any ultrafiltration membranes having nominal molecular weight limits which effectively filter pyrogens can be employed, including those containing pinholes, tears and other minor defects. Since it is only the physical structure of the membrane which removes pyrogens from aqueous solutions, any membrane made from a film-forming polymer can be employed in the practice of this invention. Suitable membrane materials include, but are not limited to, polycarbonates such as materials sold under the trade name Lexan ® by General Electric Co., polyvinyl chlorides such as the material sold under the trade name Geon 121 by B. F. Goodrich Chemical Co., polyamides such as polyhexamethylene adipamide and other polyamides known commonly as nylon E. I. duPont deNemours & Co., modacrylic copolymers, such as those sold under the trade name Dynel and formed of polyvinyl chloride and acrylonitrile, styrene-acrylic acid copolymers and the like, polysulfones such as those sold under the trade name P-1700 by Union Carbide Corp., halogenated polymers such as poly(vinylidene chloride) and poly(vinylidene fluoride) sold under the trade name Kynar by Pennsalt Chemical Corp., polyvinyl fluoride sold under the trade name Tedlar by E. I. duPont deNemours & Co., and the polyfluorohalocarbon sold under the trade name Aclar by Allied Chemical Corp., polychloroethers such as that sold under the trade name Penton by Hercules, Inc. and other similar thermoplastic polyethers, acetal polymers such as the polyformaldehyde sold under the trade name Delrin by E. I. duPont deNemours & Co. and the like, acrylic resins such as polyacrylonitrile, polymethyl methacrylate, poly-n-butyl methacrylate and the like, polyurethanes, polyimides, polybenzimidazoles, polyvinyl acetate, aromatic and aliphatic polyethers and copolymers made from monomers from which the foregoing polymers were prepared.

Since the unit size of a pyrogen is only about 20,000 molecular weight, placing two membranes having suitable nominal molecular weight limits together could potentially result in low fluxes due to the double resistance to flow. It has been found quite unexpectedly that in water pyrogens aggregate to form micelles which are much larger. As a result, a very "open" membrane, such as 100,000 NMWL, can be used effectively with acceptable fluxes. Membranes having these high nominal molecular weight limits cannot be employed, however, in the presence of some detergents and surfactants such as deoxycholate that break up the micelles. In such circumstances, membranes having much smaller nominal molecular weight limits must be used with an attendant decrease in flux.

By placing two suitable ultrafiltration membranes in intimate contact skin-to-skin, the pinholes of one are blocked by the pinhole-free area of the other reducing the volumetric flow through the pinholes on a statistical basis by the ratio of the cumulative exposed area of pinholes to the corresponding pinhole-free area of the membrane. For example, assuming that a membrane has an average pinhole concentration of one per square foot and that all pinholes are 1 millimeter in diameter, which is rather large, by placing two membranes together, the compound membranes will have a pinhole concentration of one per 10,000 square feet.

It was found that by using a skin-to-skin configuration of two 100,000 NMWL ultrafiltration membranes, 5 orders of magnitude of pyrogens could be reliably removed whereas with either a single 100,000 NMWL membrane or a single 10,000 NMWL membrane this could not be achieved. Since the membrane porosity in the skin-to-skin configuration is approximately 65 Angstrom units in diameter, pyrogens in their micellar form were effectively filtered.

It was anticipated that debris such as particles, pyrogens and pyrogen generating bacteria would accumulate in the porous substructure of the upstream ultrafiltration membrane in the skin-to-skin configuration and that as a result the permeate flux would decrease over a period of time. To avoid substantial accumulation in the substructure and to facilitate regeneration of the membranes, a third ultrafiltration membrane was placed upstream of the other two membranes with its skin surface facing upstream. This three membrane configuration proved to be superior in both pyrogen removal and throughput to the two membrane configuration described above, and thus, is the preferred configuration of this invention.

The skin-to-skin membrane configuration is preferably employed in the form of membrane packets and cassettes for use in a high volume molecular filtration cell. Such a cell is manufactured by Millipore Corp. In essence, the cell separates the feed stream, or sample, into two product streams—the retentate, which is a concentrated solution of those macromolecules that were held back by the filter, and the filtrate, which contains those smaller molecules that have passed through the filter. Separation is performed by membrane packets, each of which consists of six membranes bonded together with a support screen between them. This sandwich is designed so that the sample flows over the outside of the packet. Large molecules remain outside the packet, while smaller molecules which can pass through the membranes end up inside the packet. Because the edges of the packet are treated with a sealant, no fluid can flow from outside to inside, or vice versa, except by passing through the membranes. The cell is designed to transport fluid from the outside of the packet to one exit port, while fluid from the inside of the packet flows to another port, without mixture of the two streams. Each of the cell's four ports connects to a manifold made up of short tubes. Two of these manifolds, one above the packet and the other below the packet at the opposite end from the first, contain five tubes, while the other two manifolds contain four tubes. The two sets of manifolds are arranged so that the tubes are staggered. Each end of the membrane packet has nine holes, five of which are surrounded by sealant. The five-tube manifolds connect to the five holes surrounded by sealant, while the four-tube manifolds connect to the alternate four holds. When the membrane packet is clamped tightly between the two manifold plates, the sealant areas act as gaskets to control the fluid flow. As a result of this gasket arrangement, the five holes and the five-tube manifolds communicate only with the outside of the packet, and these manifolds carry the sample-retentate stream. Similarly, the four holes and four-tube manifolds communicate only with the inside of the packet and carry the filtrate stream.

The cell is filled with alternating layers of membrane packets and mesh-spacers. The spacers have sealant surrounding the four holes on each end thereof which correspond to those which are unsealed in the packets. This alternate sealing completes the gasket pattern. The mesh creates spaces in which the sample/retentate fluid can flow on its way across the packet. As the fluid flows horizontally through the mesh fibers, it snakes over and under the fibers in a sinuous flow pattern. This sinuous flow is a very gentle and effective way of sweeping away retained macromolecules that accumulate at the membrane surface during filtration. Such cleaning is important because the macromolecular layer, if left undisturbed, will slow the filtrate permeation rate and decrease the resolution of separation. Sinuous flow provides good cleaning even when the retentate fluid is flowing slowly, but the faster the fluid flows up to a point, the more effective the sweeping action.

The sample under pressure enters the cell via one of the five-tube manifolds and flows horizontally over the outside of the packet in a sinuous flow through the fibers of the mesh spacer. Any concentrate which remains outside the packet is formed out of the cell by the pressurized sample via the other five-tube manifold. Fluid which passes into the packet to form filtrate can leave the the cell by either four-tube manifold. Thus, there are two independent, symmetrical fluid flow paths through the cell, with the only communication between these paths being through the membranes. In terms of function, the two five-tube manifolds are equivalent, and there is not fundamental reason why the direction of sample-retentate flow should be diagonally upward or downward. The diagonally downward flow path is recommended because this arrangement sweeps particulate contaminants from the sample out of the cell more effectively. If the sample is particle-free but tends to form bubbles, the diagonally upward flow path will be more effective at removing the gas. Likewise, the two four-tube manifolds are equivalent and either can be used as the filtrate outlet with the other being sealed. The lower four-tube manifold is recommended only because it allows gravity to assist drainage.

The high volume cell containing the membrane packet is connected to several other components to form a working system. The essential elements are a pump or gas system to provide pressure, a valve or similar device to create back-pressure in the sample/retentate stream, reservoirs for the sample and products, and connecting tubing. Pressure serves the dual function of forcing the fluid to move through the cell and forcing the smaller molecules to pass through the membrane. The retentate outlet must be restricted, for example with a valve, so that the sample fluid does not rush through the cell from inlet to outlet with very little filtrate being formed. However, if a valve is used to restrict the outlet, then retentate cannot leave the cell as fast as the pump is pushing sample into the cell. As a result, pressure builds up and forces filtrate through the membrane. The more the retentate stream is restricted, the more filtrate will be formed. Thus, the back-pressure valve makes filtration possible and provides close control over the concentration factor, i.e. the ratio of filtrate flow to retentate flow.

Figure 1:
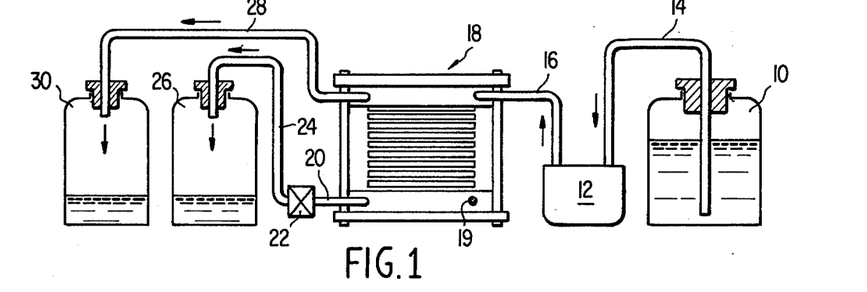
FIG. 1 is a schematic illustration of a single pass filtration set-up through a high volume molecular filtration cell.

Referring now to the drawings, FIG. 1 schematically illustrates a single-pass filtration set-up through a high volume molecular filtration cell. The sample to be filtered is contained within reservoir 10 and is pumped by pump 12 through connecting tubing 14 and 16 to high volume cell 18. Retentate is removed from cell 18 by connecting tubing 20 and 24 which is restricted by valve 22. The retentate stream is collected in reservoir 26. Filtrate is removed from the cell via connecting tubing 28 and is collected in reservoir 30. A second filtrate outlet is sealed by stopper 19.

Figure 2:
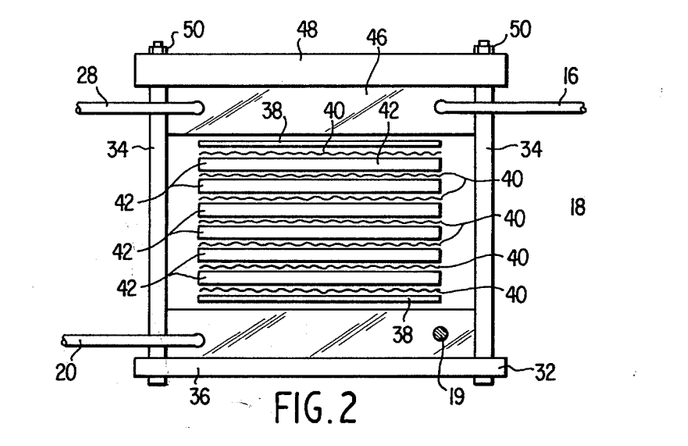
FIG. 2 is a detailed schematic representation of the high volume cell shown in FIG. 1.

FIG. 2 is a detailed schematic representation of high volume cell 18 shown in FIG. 1. Cell 18 comprises a bottom frame plate 32 having tie-rod bolts 34 extending vertically therethrough. Placed on top of plate 32 and between bolts 34 is the bottom manifold plate 36. A polyethylene gasket 38 is placed on top of manifold plate 36. A retentate spacer screen 40 is placed on top of gasket 38 and a membrane packet 42 is placed on top of screen 40. A sequence of alternating screens 40 and packets 42 is then repeated until the desired amount of membrane is in the cell. An additional screen 40 is placed on top of the stack followed by a second gasket 44. On top of the gasket 44 is placed top manifold plate 46 followed by top frame plate 48. Top nuts 50 are tightened on tie-rod bolts 34 which extend through plate 48 to hold the cell assembly firmly together.

Figure 3:
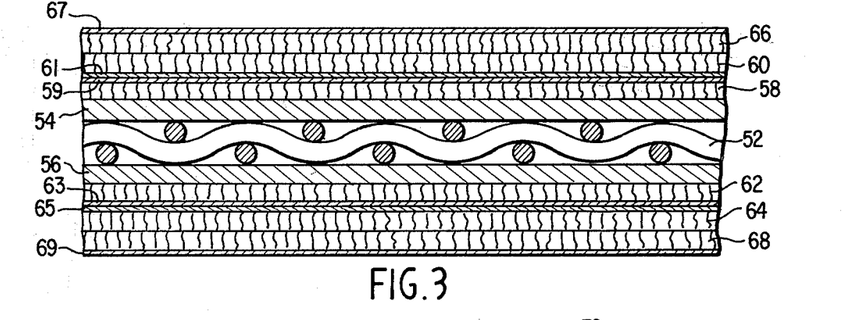
FIG. 3 is a detailed partial cross-sectional view of a membrane pocket in accordance with a preferred embodiment of the present invention.

FIG. 3 is a detailed partial cross-sectional view of a membrane packet in accordance with the preferred embodiment of the present invention. In the middle of the packet is spacer screen 52 which can be made for example of Dacron. On both sides of screen 52 are placed two sheets of paper-like non-woven support materials 54 and 56. Adjacent sheet 54 are two anisotropic ultrafiltration membranes 58 and 60 placed in a skin-to-skin configuration so that skin 59 of membrane 58 is in intimate contact with skin 61 of membrane 60. Likewise, adjacent sheet 56 are two anisotropic ultrafiltration membranes 62 and 64 placed in a skin-to-skin configuration so that skin 63 of membrane 62 is in intimate contact with skin 65 of membrane. A further anisotropic ultrafiltration membrane 66 is placed upstream of membranes 58 and 60 with its skin 67 facing in the upstream direction. Likewise, another anisotropic ultrafiltration membrane 68 is placed upstream of membranes 62 and 64 with its skin 69 facing in the upstream direction. All of the layers of this packet are sealed together around their perimeter so that the sample to be filtered can only enter the interior of the packet by passing through each set of three adjacent membranes. Although the packet is shown with three adjacent ultrafiltration membranes in accordance with the preferred embodiment of the present invention, the packet can be prepared with only two membranes in a skin-to-skin configuration on each side of the packet. Thus, ultrafiltration membranes 66 and 68 are optional.

Figure 4:
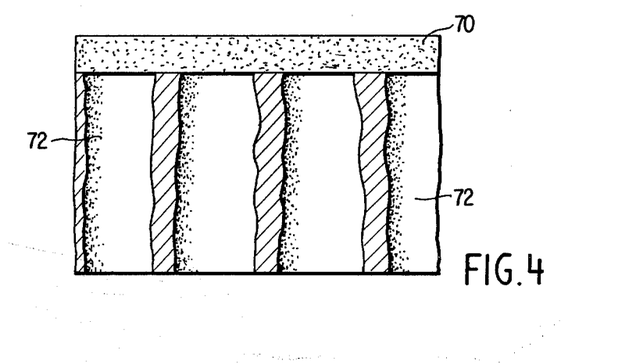
FIG. 4 is a graphic representation of part of an anisotropic ultrafiltration membrane.

FIG. 4 is a graphic representation of part of an anisotropic ultrafiltration membrane showing its highly asymmetric structure. The membrane comprises a thin skin or film 70 supported by a highly porous substructure 72. The skin 70 is very thin and is the actual molecular filtration membrane surface. The drawing is not to scale, the thickness of the skin being exaggerated for purpose of illustration.

Figure 5:
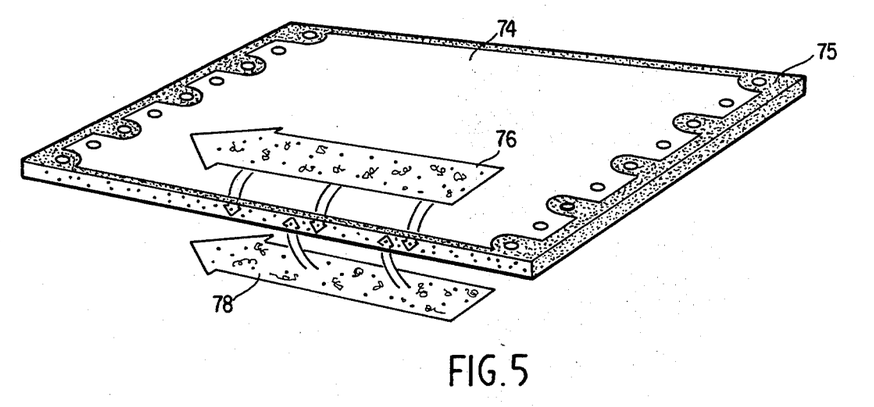
FIG. 5 is a partially cutaway perspective view of a membrane packet showing sample-retentate and filtrate flow.
Figure 6:
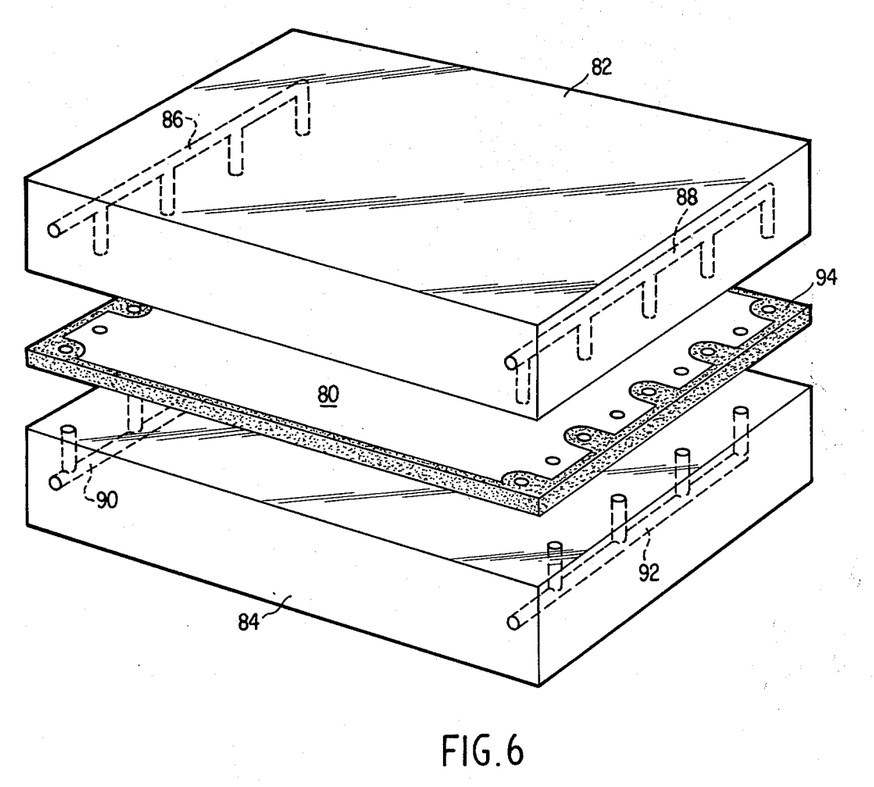
FIG. 6 is an exploded view showing the relationship between membrane packet and the manifold plates of a high volume cell.

FIG. 5 is a partially cutaway perspective view of a membrane packet such as that partially shown in FIG. 3. For simplicity, only the outersurfaces of the two membranes which face upstream are shown. The packet 74 is sealed around its entire perimeter with sealant 75 so that no fluid can flow from the outside of the packet to the inside except by passing through the membranes. The sample-retentate stream is represented by arrows 76 and 78 flowing horizontally across the outer surfaces of the membranes. Larger molecules represented by convoluted lines remain outside the packet, whereas smaller molecules represented by dots pass through the membranes to the inside of the packet. FIG. 6 is an exploded view showing the relationship between the four manifolds and a membrane packet such as that shown in FIG. 5. For simplicity, only one packet is shown and the retentate spacer screens and gaskets shown in FIG. 2 are not shown in FIG. 6. Membrane packet 80 is disposed between top manifold plate 82 and bottom manifold plate 84. Manifold plate 82 contains a manifold 86 having four tubes and a manifold 88 having five tubes. Manifold 84 contains manifold 90 having five tubes which is positioned at the opposite end of packet 80 from manifold 88, and a manifold 92 having four tubes which is positioned at the opposite end of packet 80 from manifold 86. Each end of packet 80 has nine holes, five of which are surrounded by sealant 94. When membrane packet 80 is clamped tightly between manifold plates 82 and 84, five-tube manifolds 88 and 90 connect to the five holes at each end of the packet that are surrounded by sealant, while the four-tube manifolds 86 and 92 connect to the alternate four holes at each end of the packet. The sealant areas act as gaskets to control fluid flow. The sample-retentate stream is carried by manifolds 88 and 90 which only communicate with the outside of packet 80, and the filtrate stream is carried by manifolds 86 and 92 which only communicate with the inside of packet 80.

Figure 7:
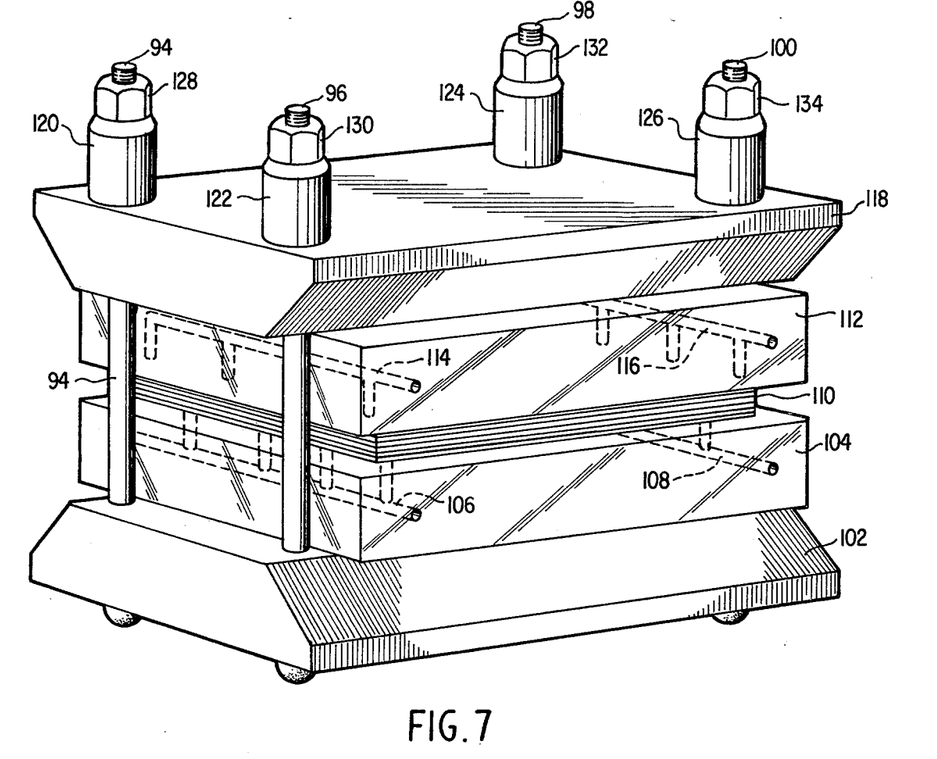
FIG. 7 is a perspective view of an assembled high volume cell.

FIG. 7 is a perspective view of an assembled high volume cell. Tie-rod bolts 94, 96, 98, and 100 extend vertically from bottom frame plate 102. Bottom manifold plate 104 is positioned on top of plate 102 with the nine holes from five-tube manifold 106 and four-tube manifold 108 facing up. The series of gaskets, retentate spacer screens, and membrane packets described with respect to FIG. 2 and designated collectively as 110 in FIG. 7 are placed over manifold plate 104 so that the holes in the gaskets, screens, packets and manifold plate are all aligned. Top manifold plate 112 is positioned over materials 110 with the nine holes from four-tube manifold 114 and five-tube manifold 116 facing down and aligned with the holes in materials 110. Top frame plate 118 is placed over bolts 94, 96, 98, and 100 on top of manifold plate 112. If needed, tie-rod spacers 120, 122, 124 and 126 are placed on the tie-rod bolts prior to placement of top nuts 128, 130, 132 and 134 on the tie-rod bolts. The nuts are tightened by means of a torque wrench to a torque of 500 in-lbs.

The operation of the high volume cell will now be described with reference to the accompanying figures. Referring to FIG. 1 in which the high volume cell 18 is shown set up for single pass operation, the system must first be checked to insure that there are no leaks between the retentate stream and the filtrate stream. This test referred to as the "bubble test" is based on the fact that a wet ultrafiltration membrane will not allow passage of gas at pressures within the operating range of the high volume cell. Water, buffer or unfiltered liquid is allowed to run slowly into the cell via sample inlet tube 16. The back pressure valve 22 should be adjusted so that the filtrate and retentate flow rates are about equal. If the temperature of the sample fluid is significantly warmer or cooler than the ambient temperature of the cell, the fluid should be allowed to continue running through the cell until the membranes are equilibrated to the sample temperature. The torque should then be rechecked because the temperature change causes the membranes to expand or contract. When fluids will necessitate a loosening of the tie-rod nuts, while cold fluids will require that the nuts be retightened. After several hundred milliliters per square foot of membrane have passed through the cell 18 so that the membranes are thoroughly wet, the flow of fluid through tubing 16 is shut off. Retentate outlet 20 is sealed by closing back-pressure valve 22. Filtrate outlet tube 28 is then submerged in liquid. A nitrogen pressure tank is connected to sample inlet tube 16 and a pressure of 2–3 psig is applied. Liquid will flow from the filtrate outlet tube 28 until all liquid has been forced out of the upstream portion of the cell. Once flow has stopped, the pressure is slowly increased until a pressure is reached which is a few psig above the pressure at which the sample is to be filtered, not to exceed 100 psig. If not bubbles appear in the filtrate manifold after approximately one minute at operating pressure, all of the seals are good. A small amount of air appearing at the filtrate outlet indicates a small leak which seldom affects the performance of the system. Vigorous bubbling from the filtrate outlet may mean that some membranes were not completely wetted, that the tie-rod nuts were not sufficiently tightened, or that there is a leak somewhere in the cell caused by cracked membranes of damaged sealing areas.

After completion of a successful bubble test, the pressure is released, the nitrogen tank disconnected from sample inlet tube 16, sample reservoir 10 is reconnected to sample inlet tube 16, and filtrate outlet tube 28 is reconnected to filtrate reservoir 30. Back-pressure valve 22 is then reopened. Before introducing the sample to the high volume cell, it should be free of particles larger than 10 microns which may clog the mesh of the retentate spacers. This can be done using an in-line prefilter or a separate batch-type filtration system.

To being filtration, pump 12 is turned on and adjusted to a predetermined operating pressure. Operating pressure can be read on a pressure gauge connected to sample inlet 16 (not shown). For most applications, optimal pressures range from 5–40 psig. Operating pressure should not exceed 100 psig. Back-pressure valve 22 is then adjusted to achieve a desired ratio between filtrate flow and retentate flow. The efficiency of molecular separation will be reduced by an increase in filtrate/retentate flow ratio. The more valve 22 is closed to increase filtrate flow, the slower the retentate will flow and the greater will be the accumulation of retained macromolecules at the membrane surface. This thickened layer of macromolecules will interfere with the passage of other molecules which should be appearing in the filtrate. The ratio between filtrate and retentate flow rates directly affects the concentration of the retentate stream. When adjusting this ratio, especially for single flow, the retentate concentration can be calculated in terms of flow rates as follows: $C_r = C_s(1 + (F_f/F_r))$, where $F_f$ and $F_r$ are filtrate and retentate flow rates, respectively, and $C_r$ and $C_s$ are the concentrations of the retentate as it leaves the cell and of the sample as it enters the cell, respectively.

Lipopolysaccharide (LPS) solution is pumped by pump 12 through sample inlet tube 16 into top manifold plate 46. Referring to FIG. 7, LPS solution enters five-tube manifold 116 in top manifold plate 112 from the inlet tube. Because the back-pressure valve restricts retentate flow out of five-tube manifold 106 in bottom manifold plate 104, the pressure forces the LPS solution horizontally across the outside of the membrane packet, as shown in FIG. 5, and forces filtrate through the membranes. Once inside the membrane packet, the filtrate can exit only by four-tube manifold 114 in top manifold plate 112 since four-tube manifold 108 in bottom manifold plate 104 is sealed. As shown in FIG. 1 and 2, the lower right-hand manifold is sealed by means of stopper 19. The filtrate having reduced pyrogen concentration passes through filtrate outlet tube 28 to filtrate reservoir 30.

Although the high volume cell has been described with respect to the use of membrane packets and retentate spacer screens, such as those illustrate in FIGS. 2 and 3, the cell can also be operated using membrane cassettes in lieu of part or all of the membrane packets. A membrane cassette is equivalent to a plurality of alternating membrane packets and retentate spacer screens placed adjacent to one another and all sealed together around their perimeter edges. In actual practice, if three membrane packets were desired, the membrane cassette would be produced by first taking a half of a membrane packet such as that shown in FIG. 3 including the spacer screen shown as 52, placing a retentate spacer screen adjacent the outer skin of the upstream ultrafiltration membrane, placing a complete membrane packet adjacent the retentate spacer screen, placing a second retentate spacer adjacent the other surface of the membrane packet, placing a second complete membrane packet adjacent the second retentate spacer screen, placing a third retentate spacer screen adjacent the other surface of the second membrane packet, and placing another half of a membrane packet including the spacer screen so that the other skin of the upstream ultrafiltration membrane is adjacent the third retentate spacer screen. When all of the holes in the retentate spacer screens and in the half and complete membrane packets are aligned, the perimeter edges of all of the screens and packets are sealed together. Because of the spacer screens on the inside of the half packets which face outward in the cassette, the cassette is used in the high volume cell with only a gasket adjacent each surface thereof. A cassette can be made from any number of packets using this procedure. The cassettes used in the following examples were made from ten packets. If it is desired to use packets and cassettes together in a high volume cell, a retentate spacer screen should not be placed between the cassette and the packet.

A more complete appreciation of the invention will be realized by reference to the following specific examples relating to specific membrane configurations and specific processes for utilizing the configurations. The following examples are not intended to limit the invention disclosed herein except to the extent that limitations are specifically stated or to the extent to which limitations appear in the appended claims. Each of the Millipore ultrafiltration membrane employed in the following examples having a designation which includes the letters PT is compatible with aqueous systems over a pH range of 1–14, including ammonium sulfate, urea and detergents, and with alcohols, up to 70% aqueous solution and aliphatic hydrocarbons. The membranes may be attacked by ketones, esters, aromatic and halogenated hydrocarbons. These membranes can be sterilized by ethylene oxide and will withstand autoclaving or steam treatment one or more times, and can be sanitized with formalin or sodium azide solutions.

EXAMPLE 1

A packet containing a PTGC ultrafiltration membrane (10,000 NMWL) without a supporting backing with full retentate screens manufactured by Millipore Corporation and having a filter area of 0.5 ft$^2$ was placed in a high volume molecular filtration cell, also made by Millipore Corporation with the tie rods tightened to a torque of 520 in-lb. A bubble test run on the filter packet yielded results of 1.4 ml/min at 10 psig and 18 ml/min at 30 psig. With a torque of 500 in-lb, the result was 16 ml/min at 30 psig. The filter packet was then challenged with a 5 µg/ml control solution of lipopolysaccharide (LPS) pumped into the cell at 21 psig with an outlet pressure of 21 psig. The retentate flow was 80 ml/min and the filtrate flow was 110 ml/min.

Pyrogenicity was measured using Mallinckrodt Pharmaceuticals Limulus amebocyte lysate PYROGENT ® for in process endotoxin detection. If endotoxins are present in quantities sufficient to result in a febrile response, they will react with the PYROGENT ® reagent to form a firm gel within the prescribed incubation period. A series of seven control solutions of known lipopolysaccharide concentration in sterile water for injection USP are prepared by diluting the 5 µg/ml control solution six times. These solutions are each aseptically dispersed into test tubes containing PYROGENT ® reagent equilibrated at 37° C. and allowed to incubate undisturbed for 60 minutes. At the end of the incubation period, each tube is observed and the results are interpreted as either positive or negative. A positive test is defined as the formation of a firm gel capable of maintaining its integrity when the test tube is inverted to 180 degrees. Such a result indicates the presence of endotoxin in sufficient quantity to elicit a febrile response if the material is injected into a patient. A negative test is characterized by the total absence of a gel or by the formation of a viscous gel which does not maintain its integrity when rotated to 180 degrees. It should be realized that endotoxin concentrations less than threshold pyrogenic level may cause flocculation, granulation and/or an increase in viscosity. Such reactions, however, are considered negative with regard to pyrogenicity. The 5 µg/ml LPS control solution was pumped through the filter packet and the filtrate was tested with the PYROGENT ® reagent. If the result was positive, the filtrate was diluted by an order of magnitude and then retested. This procedure was followed until a negative test was obtained. A more detailed description of the test can be found in Mallinckrodt Pharmaceuticals' publication MK-20298 issued May 1976 entitled "Limulus Amebocyte Lysate PYROGENT ® for In process Endotoxin Detection". The results of the test for pyrogenicity are set forth in Table I below:

TABLE I

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | + | $10^3$ |
| $5 \times 10^{-10}$ | + | $10^4$ | + | $10^4$ |
| $5 \times 10^{-11}$ | + | $10^5$ | + | $10^5$ |
| $5 \times 10^{-12}$ | − | $10^6$ | − | $10^6$ |

The membrane could not be tested with a blue dextran solution because the screens had ripped the membrane.

EXAMPLE 2

The membrane used in Example 1 was again tested without retentate screens in order to avoid any damage to the membrane. A bubble test run on the membrane gave results of 1.14 ml/min at 10 psig and 5 ml/min at 20 psig. The membrane was challenged with a 5 μg/ml solution of LPS pumped into the high volume molecular filtration cell at a pressure of 23 psig with an outlet pressure of 23 psig to give a retentate flow of 58 ml/min and a filtrate flow of 106 ml/min. After 1 liter had been pumped into the cell, a sample of the filtrate was taken to test for pyrogenicity using the procedure outlined in Example 1 above. The results obtained are listed in Table II below:

TABLE II

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | + | $10^3$ |
| $5 \times 10^{-10}$ | + | $10^4$ | + | $10^4$ |
| $5 \times 10^{-11}$ | + | $10^5$ | + | $10^5$ |
| $5 \times 10^{-12}$ | − | $10^6$ | − | $10^6$ |

The difference between the number of dilutions of the control solution required before a negative test was obtained and the number of dilutions of the filtrate required before a negative test was obtained is the number of orders of magnitude that the pyrogen concentration was reduced by the membrane packet. These results indicate that the pyrogen concentration of a control solution of $5 \times 10^{-6}$ g/ml LPS which was run through the filter packet was reduced to $5 \times 10^{-9}$ g/ml, a reduction of 3 orders of magnitude. An aqueous solution of blue dextran having a molecular weight of 2,000,000 was then run through the membrane. Pinholes plugged with blue dextran could be seen. The pinholes were small and only single dots. After blue dextran had plugged the holes, a bubble test yielded results of 0.03 ml/min at 10 psig, 0.14 ml/min at 20 psig, 6.7 ml/min at 50 psig, and 52.6 ml/min at 98 psig.

EXAMPLE 3

A packet containing a Millipore PTHK ultrafiltration membrane (100,000 NMWL) having a filter area of 0.5 ft² was placed in a high membrane volume molecular filtration cell without retentate screens. A bubble test run on the membrane gave results of 6.7 ml/min at 10 psig, 16.7 ml/min at 20 psig, 172 ml/min at 50 psig, and 1471 ml/min at 100 psig. The membrane was challenged with a 5 μg/ml solution of LPS pumped into the cell at a pressure of 20 psig with an outlet pressure of 20 psig. The retentate flow was 70 ml/min and the filtrate flow was 182 ml/min. A sample of the filtrate was taken after 1 liter of the challenge solution had been pumped into the cell and tested for pyrogenicity using the procedure of Example 1 above. The results of the test are given in Table III below.

TABLE III

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | + | $10^2$ |
| $5 \times 10^{-9}$ | + | $10^3$ | + | $10^3$ |
| $5 \times 10^{-10}$ | + | $10^4$ | + | $10^4$ |
| $5 \times 10^{-11}$ | + | $10^5$ | + | $10^5$ |
| $5 \times 10^{-12}$ | − | $10^6$ | − | $10^6$ |

The results in Table III indicate that the pyrogen concentration of the control solution was reduced by 2 orders of magnitude, since the pyrogen concentration of the $5 \times 10^{-6}$ g/ml LPS solution was reduced to the level of $5 \times 10^{-8}$ g/ml when it was run through the filter packet. An aqueous solution of blue dextran was then run through the membrane. Analysis of the membrane revealed several randomly distributed pinholes.

EXAMPLE 4

A packet containing a PTGC ultrafiltration membrane (30,000 NMWL) made by Millipore Corporation was placed in a high volume molecular filtration cell. A bubble test was run on the membrane and yielded results of 3.57 ml/min at 12 psig and 40 ml/min at 20 psig. No pyrogenicity test was run on the membrane because of the extremely high bubble test. Instead, a 0.5 percent solution of blue dextran was passed through the cell at 20 psig for 1 hour to mark any pinholes. The membrane was observed to be of poor quality with many pinholes on both sides.

EXAMPLE 5

A packet containing a Millipore PTGC ultrafiltration membrane (10,000 NMWL) with supporting backing which was modified with two unbacked Millipore PTHK (100,000 NMWL) membrane sheets facing skin-to-skin on the PTGC surfaces was placed in a Millipore high volume molecular filtration cell with full retentate screens in place. A bubble test run on the skin to skin membranes yielded results of 0.4 ml/min at 12 psig, 0.58 ml/min at 18 psig, 4.6 ml/min at 50 psig, and 11.9 ml/min at 88 psig. The membranes were challenged with a 5 μg/ml solution of LPS pumped into to the cell at a pressure of 23 psig and an outlet pressure of 21 psig. The retentate flow was 70 ml/min and the filtrate flow was 121 ml/min. The results obtained using the pyrogenicity test outlined in Example 1 above are set forth in Table IV below:

TABLE IV

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | + | $10^5$ |
| $5 \times 10^{-12}$ | − | $10^6$ | − | $10^6$ |

These results indicate that the pyrogen concentration of the control solution was reduced by 5 orders of magnitude using the modified filter packet having the skin-to-skin membrane configuration, since the pyrogen concentration of the control solution containing $5 \times 10^{-6}$ g/ml LPS was reduced to a level of $5 \times 10^{-11}$ g/ml when the solution was run through the modified filter packet.

EXAMPLE 6

A packet modified in the same way as that used in Example 5 above was prepared and placed on top of the packet used in Example 5 to make a two packet system. A bubble test run on the system gave results of 0.704 ml/min at 13 psig, 1.19 ml/min at 21 psig, 1.33 ml/min at 50 psig, and 28.6 ml/min at 87 psig. A challenge solution of 5 μg/ml of LPS was pumped into the cell at 20.5 psig with an outlet pressure of 18 psig. The retentate flow was 70 ml/min and the filtrate flow was 205 ml/min. The results obtained using the pyrogenicity test of Example 1 above are set forth in Table V below:

TABLE V

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | +− | $10^5$ |
| $5 \times 10^{-12}$ | − | $10^6$ | − | $10^6$ |

As can be seen from Table V above, the two packet system reduced by pyrogen concentration of the control solution by at least 5 orders of magnitude and close to 6 orders of magnitude, since the pyrogen concentration of the $5 \times 10^{-6}$ g/ml LPS control solution was reduced to the level of $5 \times 10^{-11}$ g/ml when run through the two packet system.

EXAMPLE 7

A packet containing a backed Millipore PTHK ultrafiltration membrane (100,000 NMWL) modified with two unbacked PTHK membrane sheets placed skin-to-skin on the PTHK surfaces was placed in a Millipore high volume molecular filtration cell with full retentate screens. A bubble test run on the membranes yielded results of 0.44 ml/min at 11 psig, 0.57 ml/min at 20 psig, 3.85 ml/min at 50 psig, and 14.7 ml/min at 86 psig. The membranes were then challenged with a 5 μg/ml solution of LPS pumped into the cell at a pressure of 24 psig with an outlet pressure of 19 psig. The retentate flow was 155 ml/min and the filtrate flow was 225 ml/min. The results obtaining using the pyrogenicity test outlined in Example 1 above are set forth in Table VI below:

TABLE VI

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | | $10^5$ |
| $5 \times 10^{-12}$ | − | $10^6$ | − | $10^6$ |

These results indicate that the modified filter packet reduced the pyrogen concentration of the control solution by 6 orders of magnitude, since the pyrogen concentration of the control solution containing $5 \times 10^{-6}$ g/ml LPS was reduced to the level of $5 \times 10^{-12}$ g/ml.

EXAMPLE 8

Ten packets containing backed Millipore PTHK ultrafiltration membrane (100,000 NMWL), each modified with two unbacked PTHK membrane sheets placed skin-to-skin on the PTHK surfaces, were placed together in laminar form and sealed around the edges with polyurethane glue to form a cassette. The cassette was then placed in a Millipore high volume molecular filtration cell and challenged with a 5 μg/ml solution of LPS pumped into the cell at a pressure of 6 psig with an outlet pressure of 0 psig. The retentate flow was 135 ml/min and the filtrate flow was 350 ml/min. After 1 liter had been pumped, a sample was tested for pyrogenicity using the test outlined in Example 1 above. The test results are given in Table VII below:

TABLE VII

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | + | $10^4$ |
| $5 \times 10^{-11}$ | + | $10^5$ | + | $10^5$ |
| $5 \times 10^{-12}$ | − | $10^6$ | − | $10^6$ |

As these results indicate, the pyrogen concentration of the control solution was reduced by 4 orders of magnitude. A bubble test was run on the cassette and yielded results of 2.14 ml/min at 10 psig, 14.7 ml/min at 20 psig, 417 ml/min at 50 psig, and 1923 ml/min at 87 psig. Since the bubble test measures air passage rather than water passage, these latter two values are higher than would be expected.

After it had been left for a week, the cassette was tightened in the cell by applying a torque of 500 in-lb to the tie rods. A bubble test was run and gave a result of 1887 ml/min at 88 psig. The cassette was then retorqued to 500 in-lb and bubble tested given a result of 1620 ml/min at 84 psig. Finally, 600 in-lb of torque was applied to the cassette and a further bubble test resulted in 1620 ml/min at 87 psig.

EXAMPLE 9

Ten packets containing backed Millipore PTHK ultrafiltration membrane (100,000) NMWL) were each modified with two unbacked sheets of PTHK membrane placed skin-to-skin on the PTHK surfaces and with outer silicone screens. A bubble test was run on each packet at approximately the same four pressures. The results are set forth in Table VIII below:

TABLE VIII

| Packet Number | Air Flow (ml/min)/ Air Pressure (psig) | Air Flow (ml/min)/ Air Pressure (psig) |
|---|---|---|
| 1 | 0.18/11 | 0.46/21 |
| 2 | 0.22/11 | 0.61/22 |
| 3 | 1.04/11 | 2.60/20 |
| 4 | 1.0/11 | 2.5/21 |
| 5 | 1.06/11 | 1.64/21 |
| 6 | 1.79/11 | 3.85/21 |
| 7 | 0.43/10 | 1.56/21 |
| 8 | 0.2/11 | 0.48/21 |
| 9 | 1.12/11 | 2.85/21 |
| 10 | 1.5/11 | 2.98/21 |
| Total | 8.54/11 | 19.53/21 |

TABLE VIII-continued

| Packet Number | Air Flow (ml/min)/ Air Pressure (psig) | Air Flow (ml/min)/ Air Pressure (psig) |
|---|---|---|
| 1 | 4.69/51 | 13.51/86 |
| 2 | 6.82/50 | 21.74/86 |
| 3 | 13.33/50 | 33.33/86 |
| 4 | 13.8/50 | 30.0/86 |
| 5 | 11.11/50 | 29.41/86 |
| 6 | 20.0/50 | 50.0/86 |
| 7 | 12.5/50 | 31.25/86 |
| 8 | 10.9/50 | 33.3/86 |
| 9 | 18.2/50 | 45.5/86 |
| 10 | 17.2/50 | 33.3/86 |
| Total | 128.55/50 | 321.34/86 |

If the ten packets were combined to form a cassette, the total flow at each of the pressures tested should be the amount given in Table VIII above. The ten packets were then combined as a cassette with silicone screens between adjacent packets with the exception of a polyurethane screen between packet nos. 1 and 2. A bubble test was then run on the cassette which gave results of 5.88 ml/min at 10 psig, 19.56 at 20 psig, 100 ml/min at 50 psig, and 450 ml/min at 86 psig. The cassette was then challenged with a 5 μg/ml solution of LPS pumped into a Millipore high volume molecular filtration cell containing the cassette at a pressure of 2.5 psig with an outlet pressure of 1.5 psig. The retentate flow was 96 ml/min and the filtrate flow was 200 ml/min. The results obtained using the pyrogenicity test outlined in Example 1 above are set forth in Table IX below:

TABLE IX

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | | $10^5$ |
| $5 \times 10^{-12}$ | − | $10^6$ | − | $10^6$ |

These results indicate that the cassette reduced the pyrogen concentration of the control solution by at least 6 orders of magnitude, since the pyrogen concentration of the $5 \times 10^{-6}$ g/ml LPS solution was reduced to a level of $5 \times 10^{-12}$ g/ml.

EXAMPLE 10

Packet nos. 1 and 2 of Example 9 above could not be separated since the middle retentate screen was polyurethane instead of silicone. The unit made by packet nos. 1 and 2 was placed in the high volume molecular filtration cell and bubble tested, giving results of 0.47 ml/min at 10 psig, 1.5 ml/min at 20 psig, 12.2 ml/min at 50 psig, and 33.3 ml/min at 86 psig. The unit was challenged with a 5 μg/ml solution of LPS pumped into the cell at a pressure of 16 psig with an outlet pressure of 14 psig. The retentate flow was 110 ml/min and the filtrate flow was 275 ml/min. The results obtained using the pyrogenicity test outlined in Example 1 above are set forth in Table X below:

TABLE X

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | | $10^5$ |
| $5 \times 10^{-12}$ | − | $10^6$ | − | $10^6$ |

Referring to these results, it can be seen that the pyrogen concentration of the control solution was reduced by 6 orders of magnitude using the double packet system.

EXAMPLE 11

Packet no. 3 of Example 9 above was placed in a Millipore high volume molecular filtration cell with outer silicone screens and challenged with a 5 μg/ml solution of lipopolysaccharide pumped into the cell at a pressure of 22 psig with an outlet pressure of 17 psig. The retentate flow was 107.5 ml/min and the filtrate flow was 294.4 ml/min. The results obtained using the pyrogenicity test outlined in Example 1 above are given in Table XI below:

TABLE XI

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | | $10^5$ |
| $5 \times 10^{-12}$ | − | $10^6$ | − | $10^6$ |

These results show a reduction in the pyrogen concentration of the control solution of 6 orders of magnitude. The pyrogen concentration of the solution containing $5 \times 10^{-6}$ g/ml LPS was reduced to a level of $5 \times 10^{-12}$ g/ml when the solution was run through the single packet.

EXAMPLE 12

Packet nos. 6 and 9 used in Example 9 above were placed in a Millipore high volume molecular filtration cell with outer silicone screens. The packets were challenged with a 5 μg/ml LPS solution pumped into the cell at a pressure of 15 psig and an outlet pressure of 13 psig. The retentate flow was 100 ml/min and the filtrate flow was 273 ml/min. The results obtained using the pyrogenicity test outlined in Example 1 above are given in Table XII below:

TABLE XII

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | +− | $10^5$ | + | $10^5$ |
| $5 \times 10^{-12}$ | − | $10^6$ | − | $10^6$ |

These results indicate that the double packet reduced the pyrogen concentration of the control solution by 5 orders of magnitude.

EXAMPLE 13

Two packets of backed Millipore PTHK ultrafiltration membrane, each modified with two unbacked sheets of PTHK membrane positioned skin-to-skin on the PTHK surfaces, were placed in a Millipore high volume molecular filtration cell. A bubble test run on the two packets yielded a result of 21 ml/min at 47 psig. Tap water prefiltered with a Millipore Rogard prefilter was passed through the two packets for 27.5 hours until they became plugged. The system was run dead ended, i.e. without any retentate flow, and a pressure regulator was installed between the Rogard prefilter and feed to the packets to prevent pressure build-up overnight. Pressure and flow data for the experiment are given in Table XIII below:

TABLE XIII

| Time (hr) | Retentate Flow (ml/min) | Filtrate Flow (ml/min) | Average Feed Pressure (psig) | Average Retentate Pressure (psig) |
|---|---|---|---|---|
| 0 | 560 | 820 | 46 | 34 |
| 0.5 | 530 | 840 | 46 | 34 |
| 2.5 | 560 | 750 | 46 | 34 |
| 3.5 | 420 | 790 | 53.5 | 43.5 |
| 4.5 | 405 | 740 | 54 | 44 |
| 21.0 | 450 | 210 | 60 | 55 |
| 22.5 | 300 | 200 | 60.5 | 58.5 |

After 22 hours, a bubble test on the two packets resulted in a flow of 8.3 ml/min at 48 psig. The membranes were then regenerated using the solutions and procedures outlined in Table XIV below with the resulting flow rates and pressures shown:

TABLE XIV

| Method of Regeneration | Retentate Flow (ml/min) | Filtrate Flow (ml/min) | Average Feed Pressure (psig) | Average Retentate Pressure (psig) |
|---|---|---|---|---|
| 1% Hypochlorite Solution | | | | |
| 30 min. back flush | 1000 | 420 | 46 | 31 |
| 30 min. front flush | 150 | 610 | 60 | 55 |
| 5 g/gal Biz Solution | | | | |
| 30 min. front flush (25° C.) | 760 | 340 | 50 | 40 |
| 30 min. back flush (50° C.) | | | | |
| 2 g/l EDTA Solution | | | | |
| 1 hr. front flush | 275 | 490 | 50 | 45 |
| 1N HNO₃ Solution | | | | |
| 15 min. front flush | 440 | 455 | 45 | 40 |
| 1 hr. back flush | 450 | 585 | 51 | 42 |
| 30 min. front flush | 860 | 465 | 46 | 32 |
| 0.5N Perchloric Acid Solution | | | | |
| 30 min. back flush | 520 | 620 | 50 | 40 |
| 1N NaOH Solution | | | | |
| 45 min. back flush | 830 | 490 | 46 | 33 |

Following regeneration of the two packets, they were challenged with a 5 $\mu$g/ml solution of LPS pumped into the cell at a pressure of 21 psig with an outlet pressure of 19 psig. The retentate flow was 117 ml/min and the filtrate flow was 293 ml/min. The results obtained using the pyrogenicity test outlined in Example 1 above are set forth in Table XV below:

TABLE XV

| Concentration (g/ml) | Control | (Dilutions) | Filtrate | (Dilutions) |
|---|---|---|---|---|
| 5 × 10⁻⁶ | +· | 10⁰ | | 10⁰ |
| 5 × 10⁻⁷ | + | 10¹ | | 10¹ |
| 5 × 10⁻⁸ | + | 10² | | 10² |
| 5 × 10⁻⁹ | + | 10³ | | 10³ |
| 5 × 10⁻¹⁰ | + | 10⁴ | | 10⁴ |
| 5 × 10⁻¹¹ | + | 10⁵ | + | 10⁵ |
| 5 × 10⁻¹² | − | 10⁶ | − | 10⁶ |

These results indicate that the regenerated packets reduced the pyrogen concentration of the control solution 5 orders of magnitude. The final retentate flow was 270 ml/min and final filtrate flow was 470 ml/min at an average feed pressure of 56 psig and an average retentate pressure of 50 psig.

EXAMPLE 14

Ten packets of backed Millipore PTHK ultrafiltration membrane were modified by placing two sheets of unbacked PTHK membrane skin-to-skin on the PTHK surfaces. The packets in laminar form were then made into a cassette by sealing the edges with General Electric's RTV-60 silicone sealant. A bubble test run on the cassette placed in a Millipore high volume molecular filtration cell yielded results of 7.3 ml/min at 10 psig, 17.2 ml/min at 20 psig, and 50 ml/min at 50 psig. The cassette was then challenged with a 50 $\mu$g/ml LPS solution pumped into the cell at a pressure of 10 psig with an outlet pressure of 4 psig. The retentate flow was 156 ml/min and the filtrate flow was 263 ml/min. The results obtained using the test for pyrogenicity outlined in Example 1 above are set forth in Table XVI below:

TABLE XVI

| Concentration (g/ml) | Control | (Dilutions) | Filtrate | (Dilutions) |
|---|---|---|---|---|
| 5 × 10⁻⁶ | + | 10⁰ | | 10⁰ |
| 5 × 10⁻⁷ | + | 10¹ | · | 10¹ |
| 5 × 10⁻⁸ | + | 10² | | 10² |
| 5 × 10⁻⁹ | + | 10³ | | 10³ |
| 5 × 10⁻¹⁰ | + | 10⁴ | | 10⁴ |
| 5 × 10⁻¹¹ | + | 10⁵ | +−− | 10⁵ |
| 5 × 10⁻¹² | − | 10⁶ | − | 10⁶ |

As these results shown, a reduction in pyrogen concentration in the control solutions of at least 5 orders of magnitude, and for all practical purposes 6 orders of magnitude, was achieved using the cassette.

EXAMPLE 15

A cassette of ten packets of backed PTHK membrane modified with unbacked PTHK membrane placed skin-to-skin as used in Example 14 above was prepared and placed in a Millipore high volume molecular filtration cell. A bubble test run on the cassette yielded results of 20 ml/min at 10 psig, 49 ml/min at 20 psig, 256 ml/min at 50 psig, and 824 ml/min at 85 psig. The cassette was challenged with a 5 $\mu$g/ml LPS solution pumped into the cell at a pressure of 6 psig with an outlet pressure of 7 psig. The retentate flow was 67 ml/min and the filtrate flow was 250 ml/min.

For comparison, a cassette of ten packets containing Millipore PTGC ultrafiltration membranes was also packed in the cell. A bubble test run on the cassette gave results of 120 ml/min at 10 psig, 306 ml/min at 20 psig, 1360 ml/min at 50 psig, and 2920 ml/min at 86 psig. The same LPS solution was pumped into the cell at a pressure of 10 psig with an outlet pressure of 10 psig. The retentate flow was 100 ml/min and the filtrate flow was 225 ml/min. The results of the pyrogenicity tests for both the skin-to-skin PTHK cassette and the PTGC cassette using the pyrogenicity test outlined in Example 1 above are set forth in Table XVII below:

TABLE XVIII

| Concentration (g/ml) | Control | (Dilutions) | Skin to Skin PTHK Cassette | (Dilutions) | PTGC Cassette | (Dilutions) |
|---|---|---|---|---|---|---|
| $5 \times 10^{-6}$ | + | $10^0$ | | $10^0$ | | $10^0$ |
| $5 \times 10^{-7}$ | + | $10^1$ | | $10^1$ | | $10^1$ |
| $5 \times 10^{-8}$ | + | $10^2$ | | $10^2$ | | $10^2$ |
| $5 \times 10^{-9}$ | + | $10^3$ | | $10^3$ | + | $10^3$ |
| $5 \times 10^{-10}$ | + | $10^4$ | | $10^4$ | + | $10^4$ |
| $5 \times 10^{-11}$ | + | $10^5$ | +− | $10^5$ | + | $10^5$ |
| $5 \times 10^{-12}$ | − | $10^6$ | − | $10^6$ | − | $10^6$ |

Referring to Table XVII above, it can be seen that the cassette having ultrafiltration membranes in the skin-to-skin configuration reduced the pyrogen concentration of the control solution by at least 5 orders of magnitude, whereas the cassette having the normal configuration only reduced the pyrogen concentration by 3 orders of magnitude.

EXAMPLE 16

A skin-to-skin PTHK cassette similar to that made in Example 14 above was prepared and placed in a Millipore high volume molecular filtration cell. Hot water was recirculated through the cassette for 2 hours at 85° C. Then the cassette was challenged with 4 liters of a 5 μg/ml polysaccharide solution heated to 85° C. A sample was taken after 3 liters had been pumped in at a pressure of 6 psig with an outlet pressure of 5 psig. At 85° C. the filtrate flow was 520 ml/min and the flux was 20 ml/min/ft²/psig. The results obtained using the test for pyrogenicity outlined in Example 1 above are given in Table XVIII below:

TABLE XVIII

| Concentration (g/ml) | Control | (Dilutions) | Filtrate | (Dilutions) |
|---|---|---|---|---|
| $5 \times 10^{-6}$ | + | $10^0$ | | $10^0$ |
| $5 \times 10^{-7}$ | + | $10^1$ | | $10^1$ |
| $5 \times 10^{-8}$ | + | $10^2$ | | $10^2$ |
| $5 \times 10^{-9}$ | + | $10^3$ | | $10^3$ |
| $5 \times 10^{-10}$ | + | $10^4$ | | $10^4$ |
| $5 \times 10^{-11}$ | + | $10^5$ | | $10^5$ |
| $5 \times 10^{-12}$ | − | $10^6$ | − | $10^6$ |

These results indicate that the cassette reduced the pyrogen concentration of the control solution by 6 orders of magnitude.

From the above examples, it can be seen that a reduction in pyrogen concentration of 5 orders of magnitude could only be effected reliably using skin-to-skin ultrafiltration membrane configurations.

It can also be seen that if a skin-to-skin PTHK cassette passed less than 10 ml/min of air when pressurized to 20 psig it could be relied upon for removal of 5 orders of magnitude of pyrogenicity from a challenge level of 5 μg/ml of lipopolysaccharide to $5 \times 10^{-11}$ g/ml or less.

What is claimed is:

1. A device for removing pyrogens, or aggregates or micelles thereof, from streams of aqueous solutions comprising at least two anisotropic ultrafiltration membranes positioned in series, said membranes having nominal molecular weight limits less than the molecular weight of the pyrogens or of the aggregates or micelles of pyrogens to be removed, wherein at least one membrane is juxtaposed with at least one other membrane so that substantially all of the skin surface of one membrane is in intimate contact with substantially all of the skin surface of the other membrane and wherein the edges of one membrane are sealed to the corresponding edges of the other membrane.

2. A device according to claim 1 wherein a third anisotropic ultrafiltration membrane is positioned in series with the intimately contacted membranes so that its skin surface faces upstream and its other surface faces the intimately contacted membranes.

3. A device according to claims 1 or 2 wherein said membranes have nominal molecular weight limits of about 100,000.

4. A membrane packet for removing pyrogens, including aggregates or micelles thereof, from streams of aqueous solutions comprising
   (a) a rectangular sheet of spacer screen,
   (b) at least two rectangular anisotropic ultrafiltration membranes positioned in series adjacent to and coextensive with each side of said spacer screen, wherein at least one membrane on each side of said spacer screen is juxtaposed with at least one other membrane on the same side of said spacer screen so that substantially all of the skin surface of one membrane is in intimate contact with substantially all of the skin surface of the other membrane,
wherein the corresponding edges of the spacer screen and the membranes on each side thereof are sealed together to form a packet, a plurality of holes through the spacer screen and membranes are spaced along two opposite edges of said packet, and sealant surrounds alternating holes of the spacer screen and membranes to form gaskets therefor, and wherein said gaskets are alternated so that some of the holes communicate with the outside membrane surfaces of the packet and the remaining holes communicate through the spacer screen with the inside membrane surfaces of the packet.

5. A packet according to claim 4 wherein a third anisotropic ultrafiltration membrane is positioned in series adjacent to and coextensive with the intimately contacted membranes on each side of said spacer screen so that its skin surface faces upstream and its other surface faces the intimately contacted membranes.

6. A packet according to claims 4 or 5 wherein said membranes have nominal molecular weight limits of about 100,000.

7. A packet according to claims 4 or 5 further comprising a rectangular sheet of non-woven support material positioned between said spacer screen and said intimately contacted membranes on each of said spacer screen.

8. A packet according to claim 7 wherein said membranes have nominal molecular weight limits of about 100,000.

9. A membrane cassette for removing pyrogens, including aggregates or micelles thereof, from streams of aqueous solutions comprising a plurality of membrane packets as defined in claims 4 or 5 positioned in series with a retentate spacer screen separating each packet from the next adjacent packet, wherein the corresponding edges of the packets and spacer screens are sealed together, the holes in each packet communicate with corresponding holes through the retentate spacer screens wherein sealant surrounds alternating holes of the retentate spacer screens to form gaskets therefor, and wherein the gaskets in said packets and the gaskets in said retentate spacer screens are alternated so that some of the holes communicate with the outside membrane surfaces of the packets and the remaining holes communicate through the inside membrane surfaces of the packets.

10. A cassette according to claim 9 wherein said membranes have nominal molecular weight limits of about 100,000.

11. A process for removing pyrogens, including aggregates or micelles thereof, from streams of aqueous solutions comprising passing a stream of an aqueous solution through a device comprising at least two anisotropic ultrafiltration membranes positioned in series, said membranes having nominal molecular weight limits less than the molecular weight of the pyrogens to be removed, wherein at least one membrane is juxtaposed with at least one other membrane so that substantially all of the skin surface of one membrane is in intimate contact with substantially all of the skin surface of the other membrane and wherein the edges of one membrane are sealed to the corresponding edges of the other membrane.

12. A process according to claim 11 wherein the stream of aqueous solution is passed initially through a third anisotropic ultrafiltration membrane which is positioned in series with the intimately contacted membranes so that its skin surface faces upstream and its other surface faces the intimately contacted membranes.

13. A process according to claims 11 or 12 wherein said membranes have nominal molecular weight limits of about 100,000.

* * * * *